United States Patent
Smith et al.

(10) Patent No.: US 9,142,055 B1
(45) Date of Patent: Sep. 22, 2015

(54) REFRACTION DETERMINATION FOR ANIMATING 3D OBJECTS

(75) Inventors: Jason Smith, San Rafael, CA (US); Kiran S. Bhat, San Francisco, CA (US)

(73) Assignee: Lucasfilm Entertainment Company Ltd., San Francisco, CA (US)

( * ) Notice: Subject to any disclaimer, the term of this patent is extended or adjusted under 35 U.S.C. 154(b) by 992 days.

(21) Appl. No.: 13/175,765

(22) Filed: Jul. 1, 2011

(51) Int. Cl.
*G06T 13/40* (2011.01)
*G06T 19/20* (2011.01)
*A61F 9/008* (2006.01)

(52) U.S. Cl.
CPC .......... *G06T 13/40* (2013.01); *G06T 19/20* (2013.01); *A61F 9/00804* (2013.01)

(58) Field of Classification Search
None
See application file for complete search history.

(56) References Cited

U.S. PATENT DOCUMENTS 6,072,496 A * 6/2000 Guenter et al. ............... 345/419
2012/0188228 A1 * 7/2012 Rhee et al. .................... 345/419

OTHER PUBLICATIONS

Miller, Hyper-Real Facial Rigging, Siggraph 2004—Maya Masters Class Seminar.*

* cited by examiner

*Primary Examiner* — Xiao Wu
*Assistant Examiner* — Yu Chen
(74) *Attorney, Agent, or Firm* — Kilpatrick Townsend & Stockton LLP

(57) ABSTRACT

This disclosure describes technology, which can be implemented as a method, apparatus, and/or computer software embodied in a computer-readable medium, capable of deforming internal geometry within an outer geometry to account for light bending due to refraction, for example, for real-time modeling of a gaze direction of a 3D computer generated character's eyes. In some implementations, internal eye geometry can be deformed to capture the effect of refraction in real-time such that the gaze direction of a 3D character's eyes can be modeled during an animation phase prior to a rendering phase in the production of a computer generated motion picture.

21 Claims, 9 Drawing Sheets

Refractive Index = 1.0
(No Deformer)

Refractive Index = 2

Refractive Index = 3

Refractive Index = 4

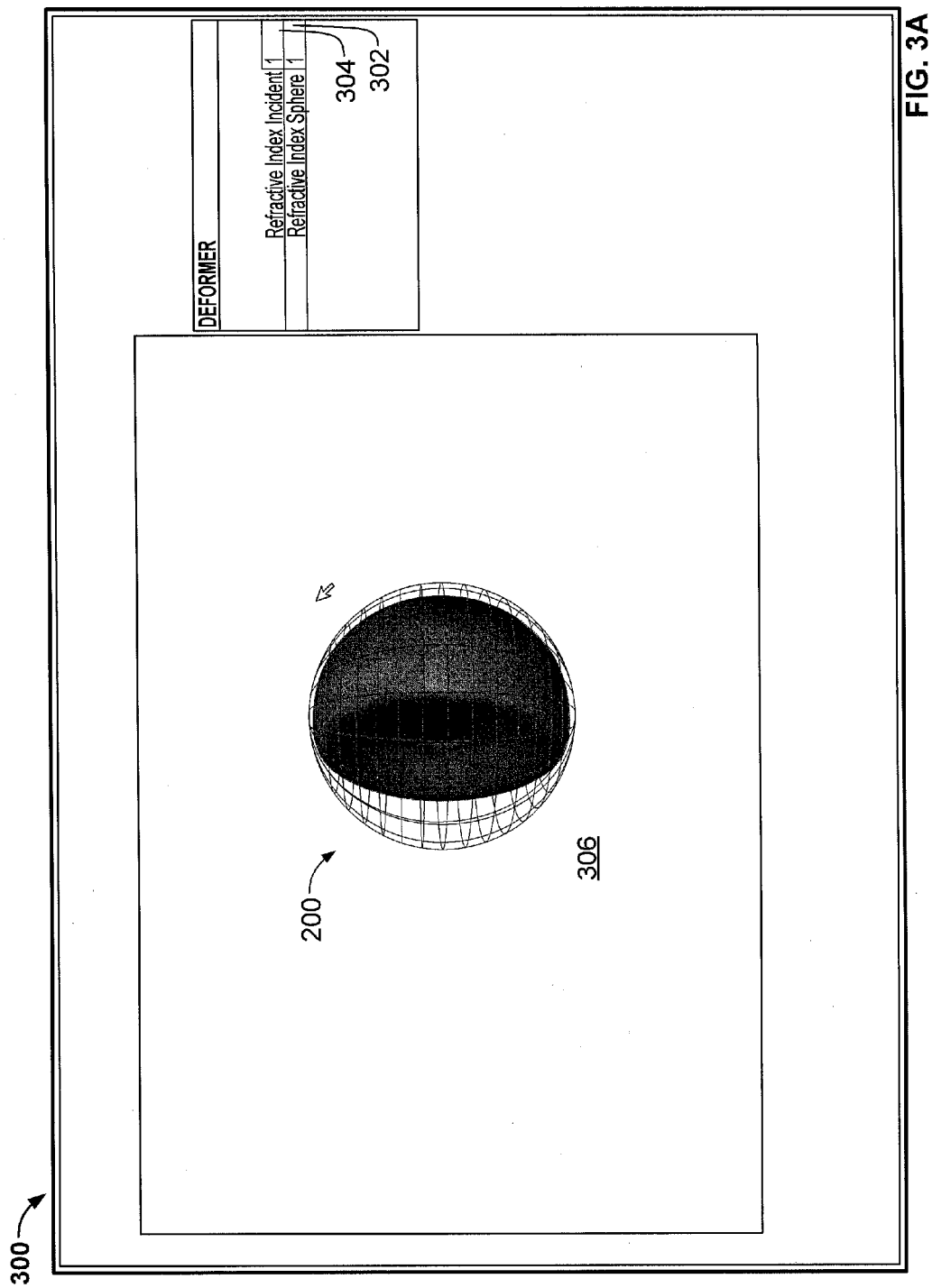

US 9,142,055 B1

REFRACTION DETERMINATION FOR ANIMATING 3D OBJECTS

TECHNICAL FIELD

This document describes technology for modeling refractive effects within a geometry, for example, for use in deforming the eyes of a three-dimensional (3D) computer generated character.

BACKGROUND

Refraction is the change in direction of a wave due to change in its speed. In optics, refraction occurs when a light wave, or ray, travels from a medium with a given refractive index to a medium with another refractive index at angle other than zero degrees or 90 degrees. Refraction is described by Snell's law, which states that the angle of incidence is related to the angle of refraction by:

$$\frac{\sin(\theta 1)}{\sin(\theta 2)} = \frac{v1}{v2} = \frac{n2}{n1}$$

where θ1 is the angle of incidence, θ2 is the angle of refraction, v1 and v2 are the wave velocities in the respective media, and n1 and n2 are the refractive indices of the respective media.

In computer graphics, most well designed computer generated (CG) characters have expressive eyes that help them engage emotionally with an audience. The eyes of a CG character can vary dramatically in their design. For example, eyes may be comprised of varying refractive indices, varying cornea sizes, and varying locations of the internal eye geometry including the pupil, iris, and lens. Big cartoony eyes may have large refraction indices. Without accounting for refraction, the internal eye geometry of such a character will appear different when viewed from a particular position than when refraction is taken into account. Moreover, because of refraction, the actual gaze direction of a character's eye depends on the relative location of the internal eye geometry with respect to a camera position and view.

SUMMARY

This disclosure describes technology, which can be implemented as a method, apparatus, and/or computer software embodied in a computer-readable medium, capable of deforming internal geometry within an outer geometry to account for light bending due to refraction, for example, for real-time modeling of a gaze direction of a 3D computer generated character's eyes. In some implementations, internal eye geometry can be deformed to capture the effect of refraction in real-time such that the gaze direction of a 3D character's eyes can be modeled during an animation phase prior to a rendering phase in the production of a computer generated motion picture.

In general, in one aspect, a method performed by one or more processes executing on a computer system includes receiving from a user of the computer system information including spherical geometry and associated internal geometry, deforming the internal geometry within the spherical geometry as viewed from a specified camera position, and displaying the spherical geometry and deformed internal geometry to the user.

This, and other aspects, can include one or more of the following features. Deforming the internal geometry can be performed in real-time and account for light bending due to refraction. The specified camera position can be received from the user of the computer system. The spherical geometry and internal geometry can each be a three-dimensional geometrical mesh. The spherical geometry can correspond to a computer generated spherical eye and the internal geometry can correspond to the internal components of the computer generated spherical eye. The method may further include deforming the internal geometry by applying a one-dimensional numerical solution to at least one point of a plurality of points associated with the internal geometry to deform the at least one point into a deformed point that accounts for light bending due to refraction within the spherical geometry. The method may further include applying the one-dimensional numerical solution to that at least one point including determining a fraction of the spherical geometry visible from the camera position, determining a quadrant within the spherical geometry where the at least one point is contained, determining the location of a point that lies on the spherical geometry by limiting the determination of the location to the fraction of the spherical geometry visible to the camera, the quadrant within the spherical geometry where the at least one point is contained, and the plane subtended by the camera position, the at least one point, and a center point associated with the spherical geometry, and determining the location of the deformed point that corresponds to the at least one point, where the determining can be based at least in part on the location of the point that lies on the spherical geometry. The method may further include determining the location of the deformed point using an affine solution to locate the deformed point along a ray that includes the camera position and the point on the spherical geometry.

In another aspect, a method performed by one or more processes executing on a computer system includes receiving from a user of the computer system information including surface geometry and associated internal geometry, deforming the internal geometry within the surface geometry as viewed from a specified camera position, and displaying the surface geometry and deformed internal geometry to the user. Other implementations of this aspect include corresponding systems, apparatus, and computer program products.

This, and other aspects, can include one or more of the following features. Deforming the internal geometry can be performed in real-time and account for light bending due to refraction. The specified camera position can be received from the user of the computer system. The surface geometry and internal geometry can each be a three-dimensional geometrical mesh. The surface geometry can correspond to a computer generated spherical eye and the internal geometry can correspond to the internal components of the computer generated spherical eye. The method can further include deforming the internal geometry by applying a one-dimensional numerical solution to at least one point of a plurality of points associated with the internal geometry to deform the at least one point into a deformed point that accounts for light bending due to refraction within the surface geometry. The method may further include determining a fraction of the surface geometry visible from the camera position, determining a quadrant within the surface geometry where the at least one point is contained, determining the location of a point that lies on the surface geometry by limiting the determination of the location to the fraction of the surface geometry visible to the camera, the quadrant within the surface geometry where the at least one point is contained, and the plane subtended by the camera position, the at least one point, and a center point associated with the surface geometry, and determining the location of the deformed point that corresponds to the at least one point, where the determining can be based at least in part on the location of the point that lies on the surface geometry. The method can further include using an affine solution to locate the deformed point along a ray that includes the camera position and the point on the surface geometry.

Potential advantages described in this disclosure may include increased efficiency in production time for a computer generated motion picture. For example, the rendering phase of a computer animated motion picture is typically performed after the completion of an animation phase, and the gaze direction of a 3D character's eyes has been finalized for the performance. However, modeling refraction for the first time during the rendering phase may lead to a large amount of wasted work since the performance might have to be reworked to accurately account for the refractive gaze change. For example, the gaze direction of a 3D character's eyes is affected by the location and direction of the pupil and iris relative to the camera. Small changes in the gaze direction of a character's eyes may result in a different facial emotion when refraction is accounted for during the rendering phase, thus resulting in less than optimal realism in the animated motion picture. Therefore, deforming the internal geometry of a 3D character's eyes during an animation phase can allow an artist to determine the proper gaze direction of the character's eyes without having to go through the more computational and time intensive rendering phase typically required to determine the gaze direction.

Further potential advantages of using a deformer to model refraction within a given geometry during an animation phase, as opposed to modeling refraction at the time of rendering, may include decoupling refractive modeling from camera & view parameters, e.g., viewport, display method, shaders, etc., that are typically required in a rendering phase. In addition, by decoupling a real-time deformer from camera & view parameters, the deformer can also be portable between 3D software packages, e.g., Zeno, Maya, Windows, Linux, etc. In some implementations, methods for real-time deforming and the real-time deformer described in this document may not require special graphics hardware for implementation, but rather can be implemented on any suitable computer system. Moreover, the computational complexity can be approximately linear to the size of the internal geometry, enabling interactive results. For example, the interactive results may be provided in real-time or near real-time.

Another potential advantage of using a deformer to model refraction within a given geometry during an animation phase can include extension to real-time modeling of refraction in a stereo manner for a 3D character. For example, a stereo pair of cameras can use the deformer to model refraction where each camera in the stereo pair can have a copy of the internal eye geometry within the eye geometry only visible from that camera, deformed based on that camera's position.

Details of one or more implementations are set forth in the accompanying drawings and the description below. Other features, aspects, and potential advantages will be apparent from the description and drawings, and from the claims.

DESCRIPTION OF DRAWINGS

FIGS. 3A-3B are examples of a run-time environment for visualizing, in real-time, the effects of refraction on internal geometry within a spherical geometry.

Like reference symbols in the various drawings indicate like elements.

DETAILED DESCRIPTION

The following disclosure, in conjunction with the figures, describes technology for deforming internal geometry within an outer geometry to account for light bending due to refraction.

Figure 1:
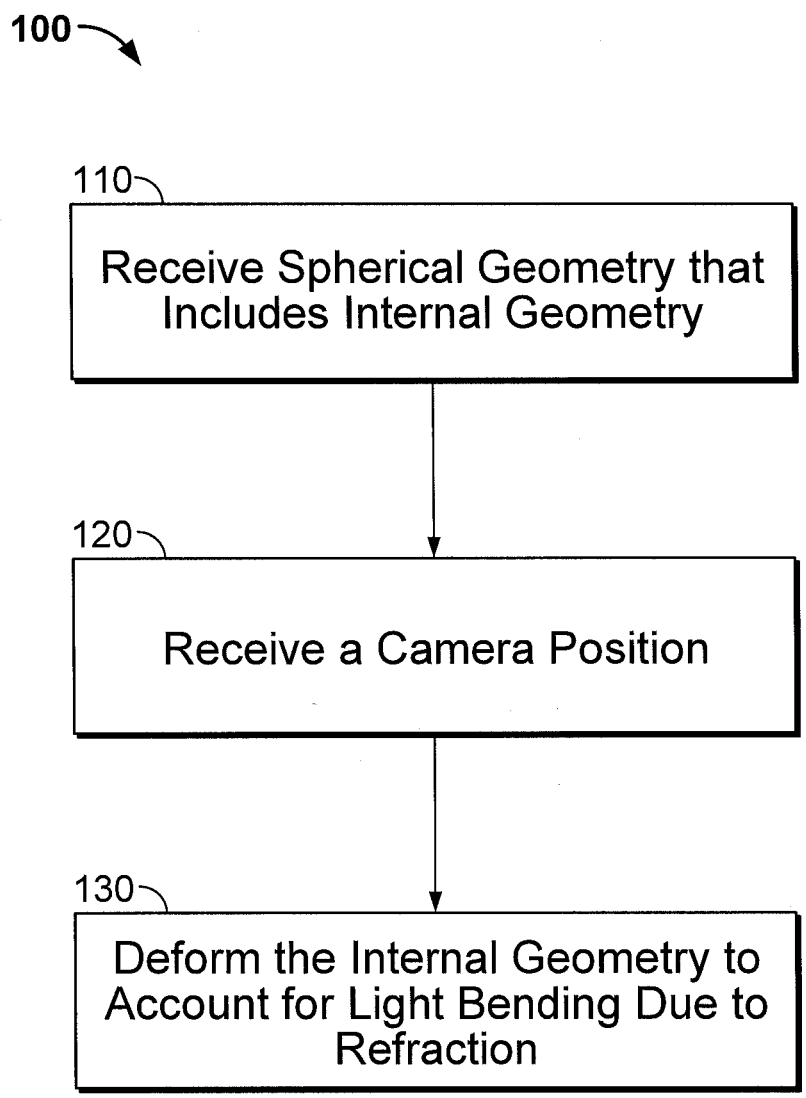
FIG. 1 is a flowchart of a method for deforming internal geometry within a spherical geometry to account for light bending due to refraction.

FIG. 1 is a flowchart of a method 100 for deforming internal geometry within a spherical geometry to account for light bending due to refraction. In some implementations, the method 100 in FIG. 1 can be performed in real-time, without intentional delay, given the processing limitations of the system and the time required to accurately measure the data, under the control of a processor or control logic in the computer system 800 during an animation phase, as opposed to a rendering phase, of a computer generated motion picture. For example, the method 100 can be incorporated into a computer program product as a real-time deformer, tangibly stored on a computer readable medium, configured to cause computer system 800 to model refraction by deforming internal geometry within a given spherical geometry viewed from a given camera in real-time.

In step 110, the method 100 receives spherical geometry that includes internal geometry within the bounds of the spherical geometry. In some implementations, the spherical geometry can be a 3D spherical mesh representing an eye or cornea of a 3D computer generated character. Such a spherical mesh may have an index of refraction associated with it that differs from the index of refraction of the surrounding environment. Similarly, the internal geometry may be a 3D mesh representing internal eye geometry. For example, the 3D internal eye geometry mesh may be representative of internal features of a 3D character's eye, such as the pupil, iris, or lens. In such implementations, both the 3D spherical mesh and 3D internal mesh can further be associated with world coordinates. For example, a mesh may be assigned a resolution such that a specific number of geometrical points are associated with the mesh. Each geometrical point may have a corresponding position in 3D space such that a 3D mesh can be formed over the geometrical points. Any appropriate mesh resolution may be selected for the spherical geometry and the internal geometry. In some implementations, any suitable discrete point based representation of the internal and spherical geometry can be used. For example, meshes, curves, points, and voxels.

In step 120, the method 100 receives a camera position. The camera position may be user specified or non-user specified. For example, a user of computer system 800 may specify a value for the camera position or, alternatively, the camera position may be determined by computer system 800 based on any suitable criteria. In some implementations, the camera position may be the world coordinates of a camera and the directional view of the camera in 3D space within a 3D environment. For example, the world coordinates of the camera may correspond to a three-dimensional X, Y, and Z position while the directional view of the camera corresponds to a vector in X, Y, Z space.

In step 130, method 100 deforms the internal geometry within the spherical geometry received in step 110 to account for light bending due to refraction as light rays travel from the medium surrounding the spherical geometry into the medium within the spherical geometry. For example, from the camera position received in step 120, there may be specific refractive effects when viewing the spherical geometry and internal geometry of a 3D character's eye. In step 130, the method 100 models the effect of refraction on the internal geometry received in step 110, as viewed from the camera position received in step 120, by deforming the internal geometry to account for light bending due to refraction. That is, as light rays move from the medium surrounding the spherical geometry to the medium within the spherical geometry, where the internal geometry is located, the light rays bend as a result of the different refractive indices of the mediums. In some implementations, deforming the internal geometry to account for light bending due to refraction allows for visualization of the effect of refraction. For example, such visualization may be available to an animator during an animation phase of a motion picture production. In some implementations, the method 100 deforms, in real-time, a 3D geometrical mesh representing internal eye geometry to account for light bending due to refraction.

Figure 2A:
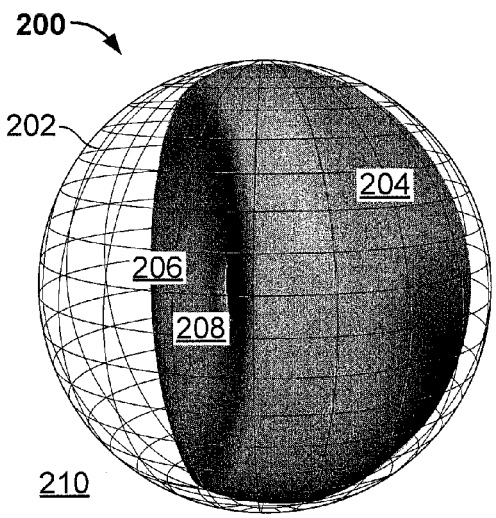
FIG. 2A is an example of a spherical eye with spherical geometry and internal geometry.

FIG. 2A is an example of a spherical eye 200 with spherical geometry 202 and internal geometry 204, the internal geometry 204 includes an iris 206 and pupil 208. In FIG. 2A, spherical eye 200 is visualized without deforming the internal geometry 204 according to method 100. That is, when visualizing spherical eye 200, the visualization does not take into account light bending due to refraction. In some implementations, in the absence of accounting for light bending due to refraction within spherical eye 200, the gaze direction of spherical eye 200 may be incorrectly determined.

Figure 2B:
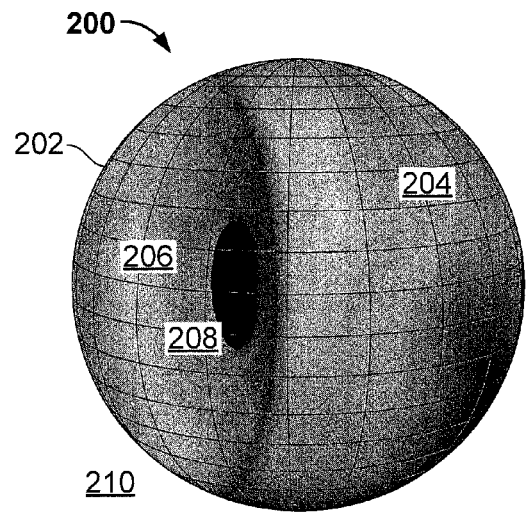
FIGS. 2B-2D are examples of internal geometry, within a spherical geometry, being deformed to account for light bending due to refraction.
Figure 2C:
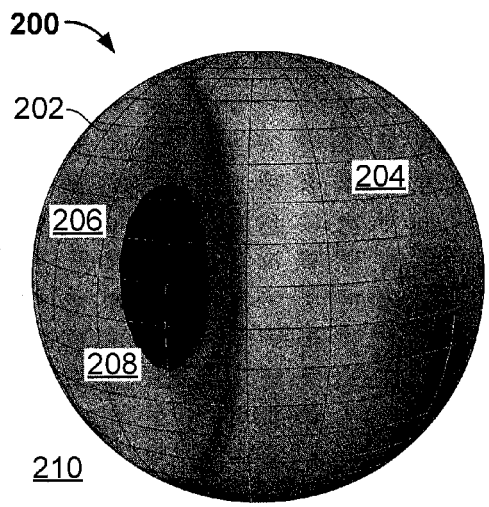
Figure 2D:
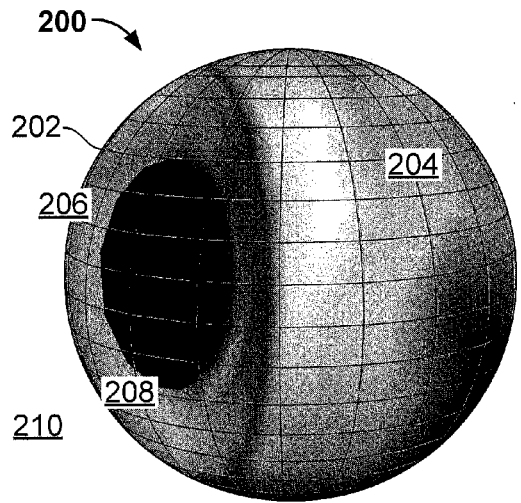

FIGS. 2B-2D are examples of spherical eye 200 being deformed in accordance with method 100. In FIGS. 2B-2D, varying refractive indices are associated with spherical eye 200. In FIGS. 2B-2D, the medium 210 surrounding spherical eye 200 has a refractive index of 1.0. In FIG. 2B, spherical eye 200 has a refractive index of 2.0. In FIG. 2C, spherical eye 200 has a refractive index of 3.0. In FIG. 2D, spherical eye 200 has a refractive index of 4.0.

To effectively visualize the gaze direction of a 3D character's eyes, the relative location of internal geometry of the eye with respect to a camera position can be determined. For example, when refraction is involved, method 100 can be implemented to determine the relative location of internal geometry within spherical geometry, with respect to a camera position, by deforming the internal geometry to account for light bending due to refraction. In FIG. 2A, the spherical eye 200 is not deformed by method 100, or in the alternative, the refractive index associated with spherical eye 200 in FIG. 2A is equal to the refractive index of the medium 210 surrounding spherical eye 200. In FIGS. 2B-2D, the spherical eye 200 is modeled by deforming the internal geometry 204 to account for light bending due to refraction within the spherical geometry 202. In some implementations, deforming internal geometry 204 in FIGS. 2B-2D results in a change in the gaze direction of spherical eye 200. For example, in FIGS. 2B-2D, the iris 206 and pupil 208 change shape, or deform, as a result of modeling refraction using method 100, thus allowing for the gaze direction of spherical eye 200 to be accurately visualized with refraction accounted for. Moreover, by modeling refraction using method 100 to deform the internal geometry 204 of the spherical eye 200, the gaze direction of a 3D character's eye may be determined during an animation phase of a motion picture production, without going through a rendering phase.

Figure 3B:
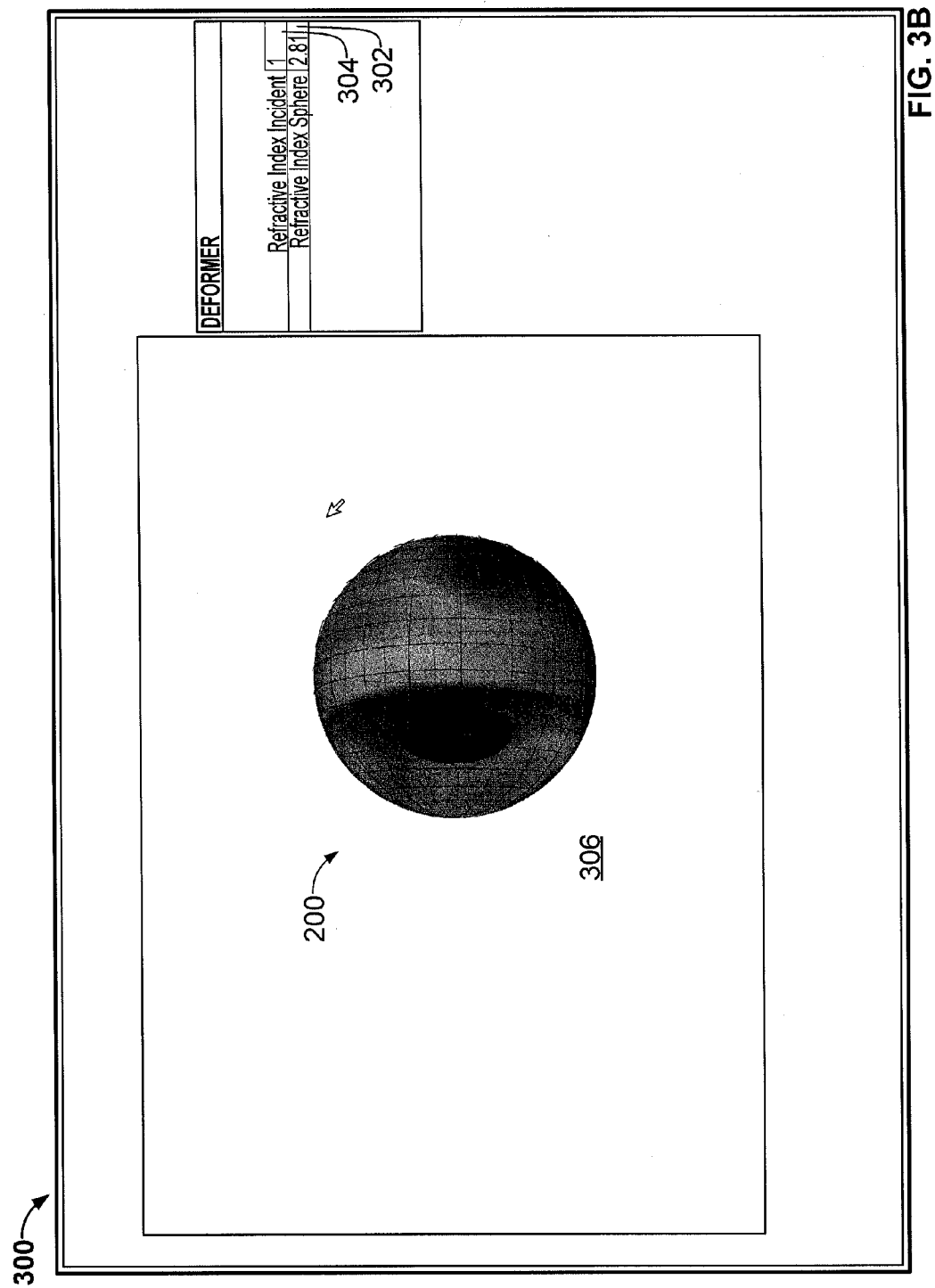

FIGS. 3A-3B are examples of a run-time environment 300 for visualizing the effect of refraction on internal geometry within a spherical geometry Run-time environment 300 may be implemented, for example, with computer system 800. In some implementations, run-time environment 300 is configured to allow visualization of spherical eye 200 with deformation applied to the internal geometry 204 of spherical eye 200 in real-time to account for light bending due to refraction according to method 100.

Run-time environment 300 may include fields 302 and 304 for inputting the refractive index of the spherical eye 200 as well as the refractive index of the medium 306 surrounding spherical eye 200.

In FIG. 3A, both the spherical eye 200 and the medium 306 surrounding the spherical eye 200 have refractive indices of 1.0. In some implementations, this is the functional equivalent of visualizing spherical eye 200 without deforming the internal geometry 204 in accordance with method 100. On the other hand, in FIG. 3B, the refractive index of the spherical eye 200 is set to 2.81 in field 302 while the refractive index of the medium surrounding the spherical eye remains at 1.0 in field 304. In FIG. 3B, the internal geometry 204 of spherical eye 200 is deformed in accordance with method 100 using a refractive index of 2.81. Run-time environment 300 in FIG. 3B provides visualization of the deformed internal geometry 204 of spherical eye 200 after taking into account light bending due to refraction as light waves travel from the medium 306 surrounding spherical eye 200 into the medium within the spherical geometry 202.

Figure 4:
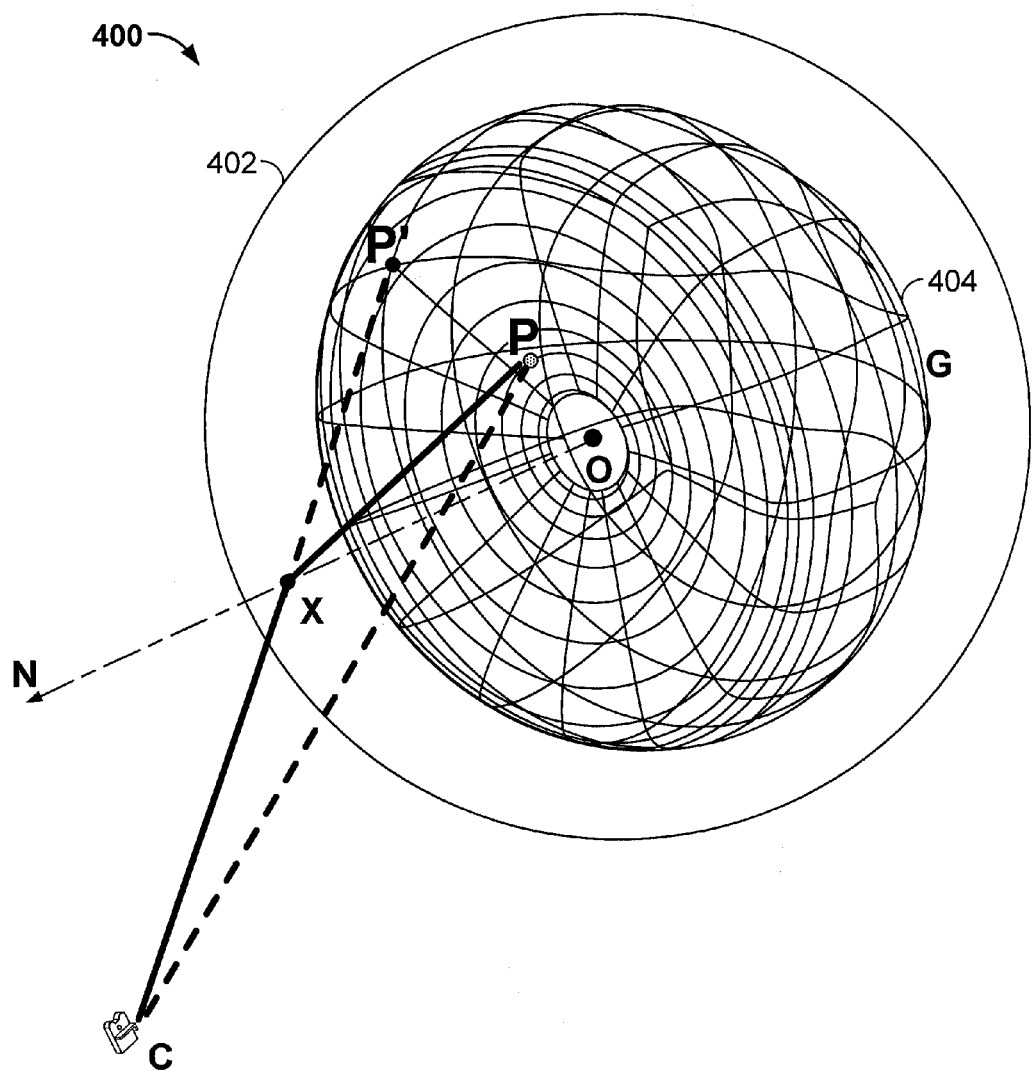
FIG. 4 is an example of a refraction framework to deform internal geometry within a spherical geometry

FIG. 4 is an example of a refraction framework 400 to deform internal geometry within a spherical geometry. For example, refraction framework 400 may include spherical geometry 402 with world coordinates O and internal geometry 404, viewed from a camera position C. In some implementations, the spherical geometry 402 includes corneal geometry of a CG character's eye and the internal geometry 404 includes internal iris and pupil geometry of the character's eye. In framework 400, P is a point on the internal geometry 404 that is to be deformed by finding a point P' that accounts for light bending due to refraction as light rays travel from the position of the camera into spherical geometry 402. In some implementations, to find deformed point P', a numerical solution may be used to solve for the point X on the spherical geometry 402 with normal N that satisfies Snell's Law:

$$\frac{\sin(\theta i)}{\sin(\theta r)} = \eta \quad (1)$$

Where $\eta$ is the index of refraction within the spherical geometry, $\theta i$ is the incident angle (i.e., the angle between CX and N), and $\theta r$ is the refracted angle (i.e., the angle between XP and −N). Upon finding the location of the point X on spherical geometry 402, deformed point P' may be determined. In some implementations, P' is found through the use of an affine solution, discussed in more detail below.

Typically, solving for a point on a sphere amounts to a 2-dimensional search for the point. For example, one solution to solve for the point X in FIG. 4 may amount to analytically solving for the point X such that equation (1) is satisfied. However, in some implementations, such an analytical solution to a 2D search problem may be overly complicated and produce numerically unstable results since there may be many solutions with no real way of knowing which solution is correct. Thus, to overcome the potential for numerically unstable results, in some implementations it may be beneficial to solve for X numerically by framing the 2D search problem for X as a 1-dimensional search for X.

Figure 5:
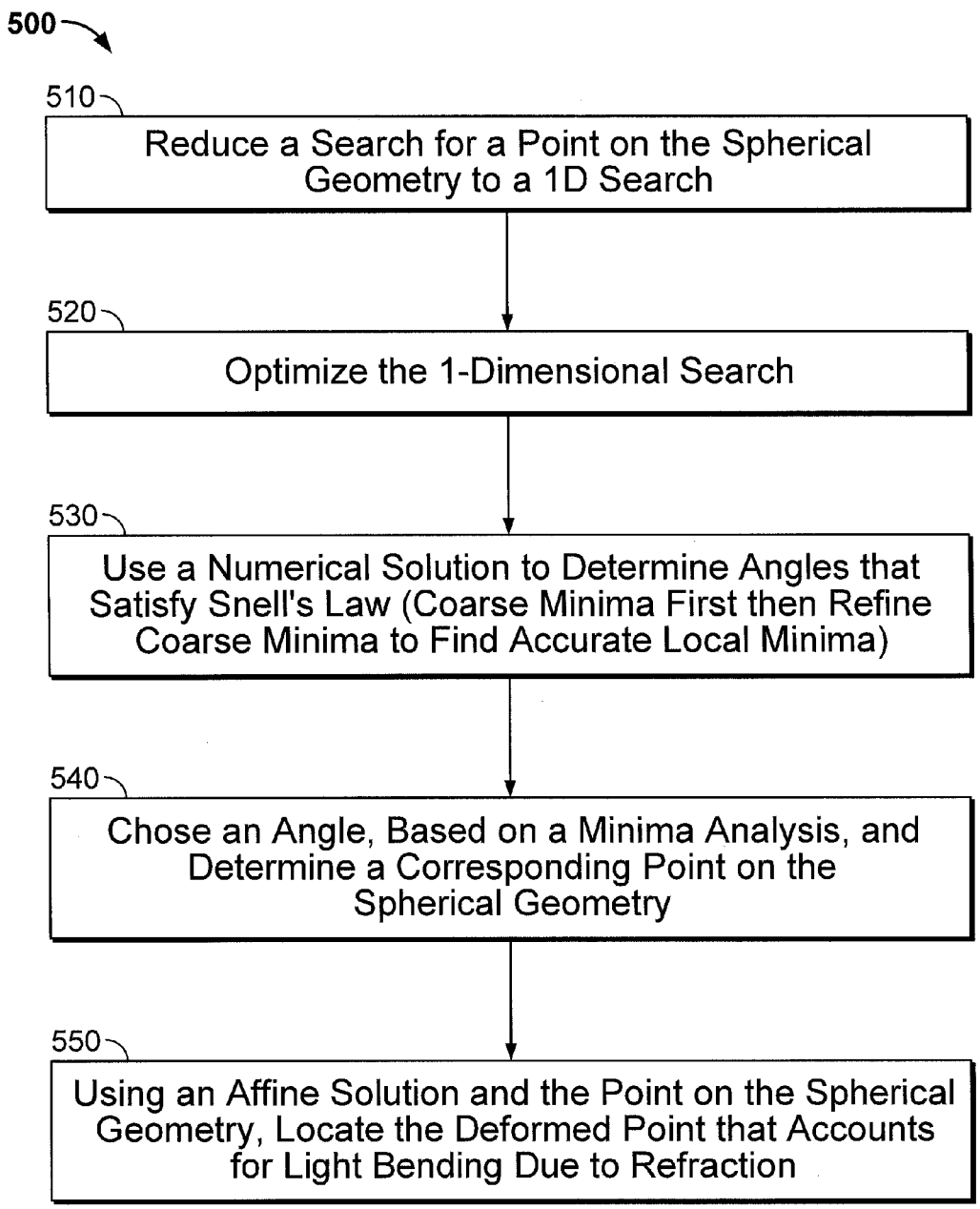
FIG. 5 is a flowchart of a method for deforming a point, in real-time, to account for light bending due to refraction.

FIG. 5 is a flowchart of method 500 for deforming a point on an internal geometry, in real-time, to account for light bending due to refraction. In some implementations, method 500 may be embodied as a numerical solution that first finds the point X on spherical geometry 402 in FIG. 4 and then, using the point X, finds the deformed point P' that accounts for light bending due to refraction. For example, in step 510, the search for the point X on the spherical geometry 402 may be reduced to a 1-dimensional search. In some implementations, several observations allow for reducing a typical 2D search problem to a 1D search problem. For example, the point X on spherical geometry 402 in FIG. 4 should lie on the plane subtended by the camera center C, the point P, and the normal N in FIG. 4. This is the geometric effect of refraction, that is, light bends when it interacts with a new medium (as determined by the index of refraction), but it stays in the same plane subtended by its original direction and surface normal at the point of interaction. In some implementations, given that the normal N of a sphere passes through the sphere center O, the point X lies in the plane subtended by C, P, and O. For example, X will lie on a circular slice of spherical geometry 402 corresponding to the plane subtended by C, P, and O.

In some implementations, optimizations may be made to method 500 to increase the efficiency for determining a solution to the 1D search for the point X on spherical geometry 402. For example, in step 520, optimizations may include determining the fraction of the spherical geometry 402 that includes the point P on the internal geometry 404. That is, the 1-dimensional search for X can be restricted to the part of the spherical geometry 402 visible from the camera C. Additionally, within this visible part, searching for X can further be limited in step 520 to the quadrant of the spherical geometry 402 above the line CO that contains the point P. For example, the solution space for X can be reduced to the section of the sphere such that the deformed point P' can be in the quadrant of the sphere ranging from the middle of the spherical geometry 402 to the edge of the spherical geometry 402 in the direction of the point P.

In addition to elimination spurious solutions, restricting the search region has the added benefit of increasing the overall search speed.

After reducing the search for the point X on the spherical geometry 402 to a 1D search problem in step 510 and optimizing the solution space for X in step 520, a numerical solution can be used to find the location of the point X by searching for the angle alpha (shown in FIG. 6) that satisfies equation (1).

In some implementations, it is useful to distinguish between two types of points on an internal geometry that will be deformed, e.g., visible points and invisible points. The visible points have two or three valid roots, e.g., solutions with an error less than 1e-03, whereas the invisible points do not have a root but have a single local minimum, e.g., a solution with an error around 0.5 or more. As the direction of the camera changes relative to the spherical geometry, some of the invisible points cross the horizon line and become visible points and vice-versa. It may be important to handle this transition smoothly; otherwise flicker around the horizon line may be visible wherever there is any relative motion between the camera and the spherical geometry.

Figure 6:
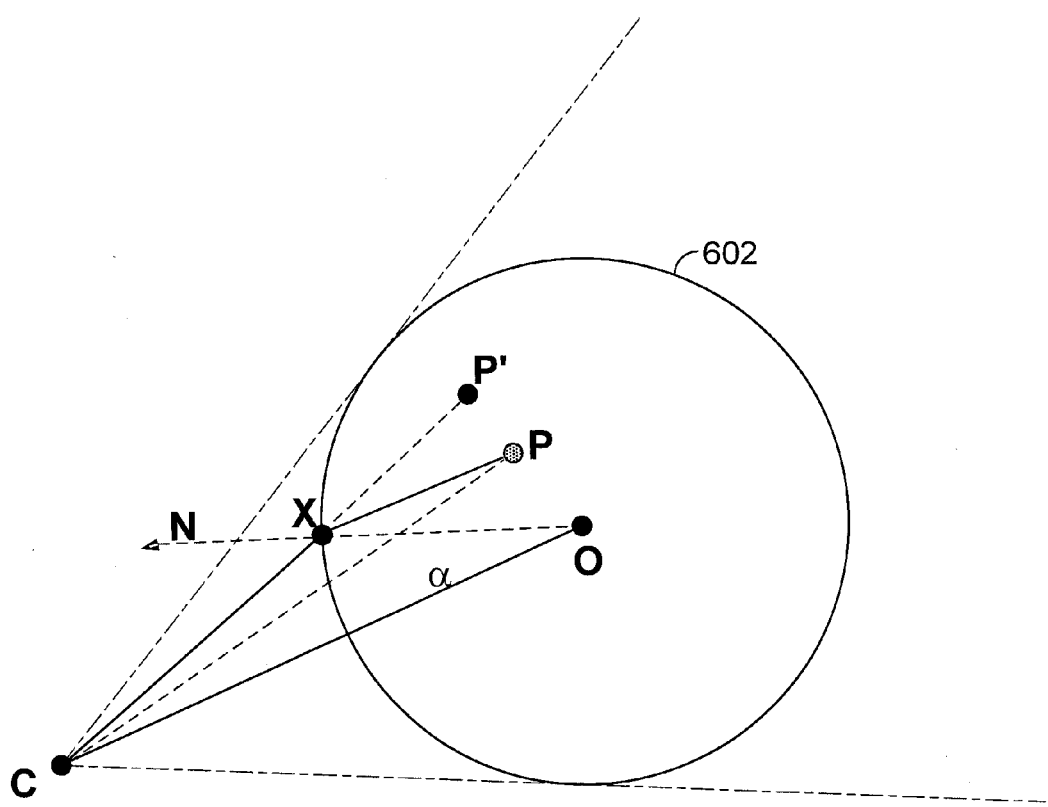
FIG. 6 shows a circular slice of a spherical geometry.

FIG. 6 shows a circular slice 602 of spherical geometry 402, parameterized by the angle alpha ($\alpha$), produced from the intersection between the visible portion of the spherical geometry 402 and the plane subtended by the camera C, point P, and spherical center O. In step 530 of FIG. 5, a numerical solution may be used to determine an angle, or multiple angles, that satisfy equation (1). For example, a discrete optimization may include sampling a pre-determined number of alpha values between the edges of the circular slice 602. The number of pre-determined alpha values may, for example, be an arbitrary number of values based on the capabilities of a computing system. In step 530, for each alpha value sampled, the error between the sample and equation (1) can be found. In step 530, as the error associated with each alpha value is determined, minima associated with the error may be encountered.

In step 530, some implementations may further refine the minima encountered at the alpha value with the lowest error between the sample and equation (1). For example, continuous optimization such as a bisection or secant method may be used to further refine the minima encountered to find an accurate local minima associated with the alpha value.

In some implementations, solving for the point X on spherical geometry 402 may yield multiple potential roots. For example, two valid minima and one reflected solution. In step 540, a reflected solution can be detected through any suitable technique and removed from the solution space. For example, incoming and refracted angles should share the same cross product direction; a reflected solution will have a flipped cross product and thus can be removed from the solution space. The question may remain though as to how to choose the correct minima among two valid solutions. If a minima is selected at random, in some implementations there will be noticeable flicker around the horizon line of the spherical geometry 402, especially when the camera is moved relative to the spherical geometry. In some implementations, choosing the solution with lower alpha value produces the most temporally consistent results with minimum flickering when the camera is moved relative to the spherical geometry. This intuition stems from Fermat's principal of least time, from optics, which states that lights takes the minimum path between two points. Some points just outside the visible range, especially near the horizon, also exhibit a single minimum, although not a true root.

Figure 7:
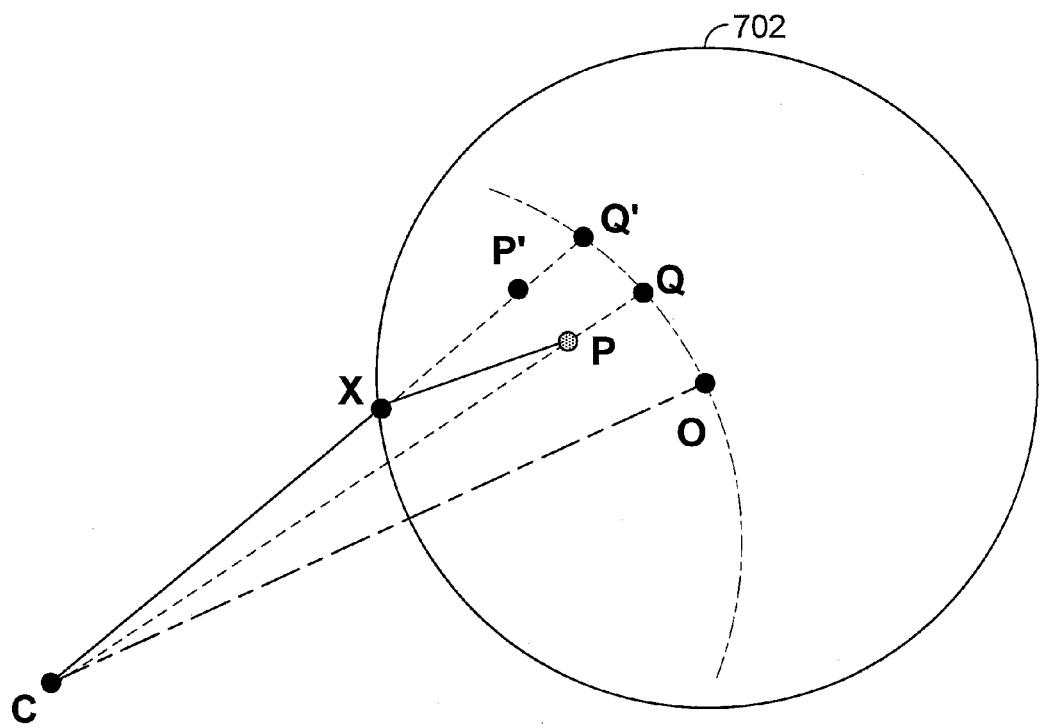
FIG. 7 shows a circular slice of a spherical geometry.

With a chosen minima and corresponding alpha value determined in step 540, in step 550 the point P on internal geometry 404 can be deformed to find the point P' such that P' is viewed from the camera C somewhere along the ray from the camera C to the intersection of the chosen alpha solution vector and the spherical geometry, for example the point X in FIG. 4, FIG. 6, and FIG. 7.

In step 550, the location on the internal geometry 404 corresponding to deformed point P' can be computed using an affine solution. For example, after computing the location of X on the spherical geometry 402 in step 540, the location of P' can be found along the ray CX. Referring to FIG. 7, in some implementations, the location of P' can be found by using the affine solution CP/CQ=CP'/CQ', where Q and Q' are obtained by tracing an arc of length CO centered at C.

Figure 8:
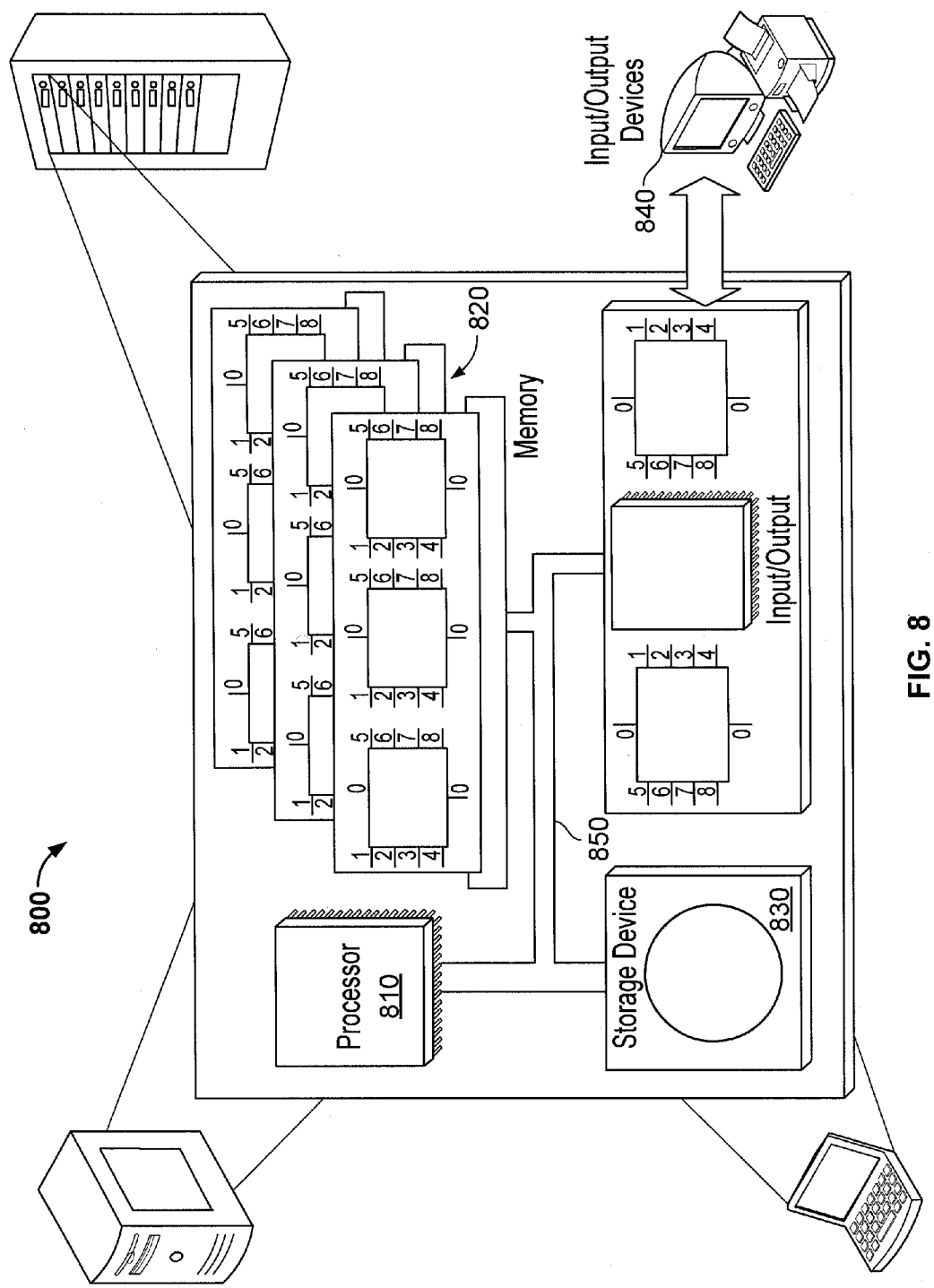
FIG. 8 is a schematic diagram of an exemplary computing system.

FIG. 8 is schematic diagram of an exemplary computing system 800. The system 800 includes a processor 810, a memory 820, a storage device 830, and an input/output device 840. Each of the components 810, 820, 830, and 840 are interconnected using a system bus 850. The processor 810 is capable of processing instructions for execution within the system 800. In some implementations, the processor 810 is a single-threaded processor. In some implementations, the processor 810 may be a multi-threaded processor. The processor 810 is capable of processing instructions stored in the memory 820 or on the storage device 830 to display graphical information for a user interface on the input/output device 840.

The memory 820 stores information within the system 800. In some implementations, the memory 820 is a computer-readable medium. In some implementations, the memory 820 is a volatile memory unit. In some implementations, the memory 820 is a non-volatile memory unit.

The storage device 830 is capable of providing mass storage for the system 830. In some implementations, the storage device 830 is a computer-readable medium. In various different implementations, the storage device 830 may be a floppy disk device, a hard disk device, an optical disk device, or a tape device.

The input/output device 840 provides input/output operations for the system 800. In some implementations, the input/output device 840 can include a keyboard, a pointing device (e.g., a mouse), and a 3D motion controller. In some implementations, the input/output device 840 includes a display unit for displaying graphical user interfaces.

The features described in this disclosure can be implemented in digital electronic circuitry, or in computer hardware, firmware, software, or in combinations of them. The apparatus can be implemented in a computer program product tangibly embodied in an information carrier, e.g., in a machine-readable storage device or in a propagated signal, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A compute program is a set of instruction that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessor, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disk; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard or keypad and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected to any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Nevertheless, it will be understood that various modifications may be made. For example, although the foregoing description focuses on the case of deforming internal geometry within a spherical geometry (e.g., a cornea), the foregoing techniques may be applicable to non-spherical planar surfaces and/or any other appropriate surface geometry, including implicit or mathematical surfaces and more general representations such as subdivision surfaces or non-uniform rational basis spline ("NURBS") surfaces. In addition, while the examples described herein discuss deforming internal geometry (e.g., iris and pupil) within spherical eye geometry, in some examples internal geometry within any appropriate surface geometry may still be deformed in accordance with the teachings of this disclosure. For example, although the foregoing description focuses on internal eye geometry, the foregoing techniques may be applicable to internal planar surfaces and/or any other appropriate internal surface geometry, including implicit or mathematical surfaces and more general representations such as subdivision surfaces or NURBS surfaces.

In addition, other steps may be provided, or steps may be eliminated, from the described flows, and other components may be added to, or removed from, the described systems. Accordingly, other implementations are within the scope of the following claims.

What is claimed is:

1. A method, performed by one or more processes executing on a computer system, the method comprising:
   receiving, by the computer system, information including a spherical geometry and an associated internal geometry, wherein the internal geometry comprises a plurality of mesh vertices, and the plurality of mesh vertices comprises a vertex at a first position;
   applying a one-dimensional numerical solution to determine a location of a point that is (i) on the spherical geometry, and (ii) in a plane defined by a specified camera position, the vertex, and a surface normal on the spherical geometry at the point;

determining a second position for the vertex using the location of the point, wherein the second position accounts for simulated light refracting as the simulated light passes through the spherical geometry as viewed from the specified camera position;

deforming the internal geometry within the spherical geometry such that the vertex is moved from the first position to the second position; and causing the spherical geometry and deformed internal geometry to be displayed on a display device prior to rendering the internal geometry.

2. The method of claim 1 wherein deforming the internal geometry is performed in real-time.

3. The method of claim 1 further comprising receiving an input that comprises the specified camera position.

4. The method of claim 1 wherein the spherical geometry and internal geometry are each three-dimensional geometrical meshes.

5. The method of claim 1 wherein the spherical geometry corresponds to a computer generated spherical eye and the internal geometry corresponds to the internal components of the computer generated spherical eye.

6. The method of claim 1 further comprising:
determining a fraction of the spherical geometry visible from the specified camera position;
determining a quadrant within the spherical geometry where the vertex is contained; and
limiting the one-dimensional numerical solution to the fraction of the spherical geometry visible from the specified camera position and the quadrant within the spherical geometry where the vertex is contained.

7. The method of claim 1 wherein determining the second position for the vertex using the location of the point comprises:
using an affine solution to locate the second position along a ray that includes the specified camera position and the point.

8. A non-transitory computer program product, encoded on a computer-readable medium, operable to cause a data processing apparatus to perform operations comprising:
receiving, by the computer system, information including a spherical geometry and an associated internal geometry, wherein the internal geometry comprises a plurality of mesh vertices, and the plurality of mesh vertices comprises a vertex at a first position;
applying a one-dimensional numerical solution to determine a location of a point that is (i) on the spherical geometry, and (ii) in a plane defined by a specified camera position, the vertex, and a surface normal on the spherical geometry at the point;
determining a second position for the vertex using the location of the point, wherein the second position accounts for simulated light refracting as the simulated light passes through the spherical geometry as viewed from the specified camera position;
deforming the internal geometry within the spherical geometry such that the vertex is moved from the first position to the second position; and
causing the spherical geometry and deformed internal geometry to be displayed on a display device prior to rendering the internal geometry.

9. The non-transitory computer program product of claim 8 wherein deforming the internal geometry is performed in real-time.

10. The non-transitory computer program product of claim 8 operable to cause a data processing apparatus to perform operations further comprising receiving an input that comprises the specified camera position.

11. The non-transitory computer program product of claim 8 wherein the spherical geometry and internal geometry are each three-dimensional geometrical meshes.

12. The non-transitory computer program product of claim 8 wherein the spherical geometry corresponds to a computer generated spherical eye and the internal geometry corresponds to the internal components of the computer generated spherical eye.

13. The non-transitory computer program product of claim 8 further comprising:
determining a fraction of the spherical geometry visible from the specified camera position;
determining a quadrant within the spherical geometry where the vertex is contained; and
limiting the one-dimensional numerical solution to the fraction of the spherical geometry visible from the specified camera position and the quadrant within the spherical geometry where the vertex is contained.

14. The non-transitory computer program product of claim 8 wherein determining the second position for the vertex using the location of the point comprises:
using an affine solution to locate the second position along a ray that includes the specified camera position and the point.

15. A system comprising:
a processor; and
a computer program product encoded a non-transitory computer-readable medium, the computer program product configured to cause the processor to perform the operations comprising:
receiving, by the computer system, information including a spherical geometry and an associated internal geometry, wherein the internal geometry comprises a plurality of mesh vertices, and the plurality of mesh vertices comprises a vertex at a first position;
applying a one-dimensional numerical solution to determine a location of a point that is (i) on the spherical geometry, and (ii) in a plane defined by a specified camera position, the vertex, and a surface normal on the spherical geometry at the point;
determining a second position for the vertex using the location of the point, wherein the second position accounts for simulated light refracting as the simulated light passes through the spherical geometry as viewed from the specified camera position;
deforming the internal geometry within the spherical geometry such that the vertex is moved from the first position to the second position; and
causing the spherical geometry and deformed internal geometry to be displayed on a display device prior to rendering the internal geometry.

16. The system of claim 15 wherein deforming the internal geometry is performed in real-time.

17. The system of claim 15 wherein the computer program product is configured to cause the processor to perform the operations further comprising receiving an input that comprises the specified camera position.

18. The system of claim 15 wherein the spherical geometry and internal geometry are each three-dimensional geometrical meshes.

19. The system of claim 15 wherein the spherical geometry corresponds to a computer generated spherical eye and the internal geometry corresponds to the internal components of the computer generated spherical eye.

20. The system of claim 15 further comprising:
   determining a fraction of the spherical geometry visible from the specified camera position;
   determining a quadrant within the spherical geometry where the vertex is contained; and
   limiting the one-dimensional numerical solution to the fraction of the spherical geometry visible from the specified camera position and the quadrant within the spherical geometry where the vertex is contained.

21. The system of claim 15 wherein determining the second position for the vertex using the location of the point comprises:
   using an affine solution to locate the second position along a ray that includes the specified camera position and the point.

* * * * *